United States Patent [19]

Fletcher et al.

[11] 4,052,666
[45] Oct. 4, 1977

[54] REMOTE SENSING OF VEGETATION AND SOIL USING MICROWAVE ELLIPSOMETRY

[76] Inventors: James C. Fletcher, Administrator of the National Aeronautics and Space Administration, with respect to an invention of; Siegfried O. Auer, Lanham; John B. Schutt, Silver Spring, both of Md.

[21] Appl. No.: 677,352

[22] Filed: Apr. 15, 1976

[51] Int. Cl.² ............................................. G01R 27/04
[52] U.S. Cl. ................................................ 324/58.5 B
[58] Field of Search ............ 324/58.5 B, 58 B, 58.5 A

[56] References Cited

U.S. PATENT DOCUMENTS

| | | | |
|---|---|---|---|
| 2,640,190 | 5/1953 | Rines | 324/58.5 B |
| 3,093,825 | 6/1963 | Allen | 324/58.5 B X |
| 3,133,246 | 5/1964 | Jaffee et al. | 324/58.5 B |
| 3,144,601 | 8/1964 | Slabodsky | 324/58.5 B |
| 3,534,260 | 10/1970 | Walker | 324/58.5 A |
| 3,629,698 | 12/1971 | Lamb | 324/58.5 B |
| 3,688,189 | 8/1972 | Lamb | 324/58.5 B |

*Primary Examiner*—Stanley T. Krawczewicz
*Attorney, Agent, or Firm*—John R. Tresansky; Robert D. Marchant; John R. Manning

[57] ABSTRACT

A method of determining vegetation height and water content of vegetation from the intensity and state of elliptical polarization of a reflected train of microwaves. The method comprises the steps of reflecting a circularly polarized train of microwaves from vegetation at a predetermined angle of incidence, detecting the reflected train of microwaves, determining the ratio of the intensities of the electric field vector components, measuring the phase difference of the components, and computing the refractive index and thickness of the layer of vegetation from a formula, wherein the refractive index is given essentially by the water content of the vegetation.

2 Claims, 2 Drawing Figures

REMOTE SENSING OF VEGETATION AND SOIL USING MICROWAVE ELLIPSOMETRY

ORIGIN OF THE INVENTION

The invention described herein was made in the performance of work under a NASA Contract and by an employee of the United States Government and is subject to the provisions of Section 305 of the National Aeronautics and Space Act of 1958, Public Law 85-568 (72 Stat. 435; 42 USC 2457), and may be manufactured and used by or for the Government for governmental purposes without the payment of any royalties thereon or therefor.

BACKGROUND OF THE INVENTION

1. Field of the Invention

The present invention relates generally to the examination of the surface reflection of polarized electromagnetic wave radiation, and more particularly to the use of surface reflection of polarized electromagnetic radiation to determine the properties of materials on or near the earth's surface.

2. Description of the Prior Art

Radar imaging, because it can be obtained through cloud cover, at night, over large areas, and with high spacial resolution has been utilized for the remote sensing of agricultural conditions from aircraft or spacecraft. Empirical attempts have been made to correlate soil moisture with signal strength, and to differentiate between fields of different crops by measuring the characteristic radar return at fixed frequencies and at vertically or horizontally oriented linear polarizations. However, no simple and straightforward remote sensing method exists in the prior art for measuring the refractive index of the soil, which is indicative of soil moisture; the refractive index of the vegetation, which is indicative of the water content of the vegetation; and the height of the vegetation.

BRIEF SUMMARY OF THE INVENTION

It is therefore one object of the present invention to provide an improved method of remote sensing of vegetation and soil.

It is another object of the present invention to provide an improved method of remote sensing of vegetation and soil for determining the soil moisture.

It is yet another object of the present invention to provide an improved method of remote sensing of vegetation and soil for determining the type and water content of the vegetation.

It is a further object of the present invention to provide an improved method of remote sensing of vegetation and soil for measuring the height of the vegetation.

The objects of the present invention are achieved in one aspect by a method of determining the water content and thickness of a layer of vegetation on a soil substrate of known refractive index $n_m$. The method comprises the steps of reflecting a circularly polarized train of microwaves of wave length $\lambda$ from the vegetation at a predetermined angle of incidence $\theta$, detecting the reflected train of microwaves, determining the ratio $I_r^p/I_r^s$ of the intensities of the orthogonal components of the electric field of the reflected train of microwaves in the plane of incidence and normal to it, measuring the phase difference $90° + \Delta$ of the components of the electric field of the reflected train of microwaves, and computing the refractive index $n_f$ and the thickness $d$ of the layer of vegetation from the formula $$\frac{I_r^p}{I_r^s} e^{i\Delta} = \frac{\left[r_f^p + r_m^p \exp(-i4\pi\sqrt{n_f^2 - \sin^2\theta}\, d/\lambda)\right]}{\left[1 + r_f^p r_m^p \exp(-i4\pi\sqrt{n_f^2 - \sin^2\theta}\, d/\lambda)\right]} \cdot \frac{\left[1 + r_f^s r_m^s \exp(-i4\pi\sqrt{n_f^2 - \sin^2\theta}\, d/\lambda)\right]}{\left[r_f^s r_m^s \exp(-i4\pi\sqrt{n_f^2 - \sin^2\theta}\, d/\lambda)\right]}$$

In the formula, $r_f^p$, $r_m^p$, $r_f^s$, and $r_m^s$ are Fresnel coefficients and are functions of $\theta$, $\lambda$, $d$, $n_f$ and $n_m$ and the refractive index of the vegetation $n_f$ is given essentially by the water content of the vegetation.

In another aspect, the present invention relates to a method of determining the moisture of a soil substrate. The method comprises the steps of reflecting a circularly polarized train of microwaves of wave length $\lambda$ from the soil substrate at a predetermined angle of incidence $\theta$, detecting the reflected train of microwaves, determining the ratio $I_r^p/I_r^s$ of the intensities of the orthogonal components of the electric field of the reflected train of microwaves in the plane of incidence and normal to it, measuring the phase difference $90° + \Delta$ of the components of the electric field of the reflected train of microwaves, and computing the refractive index $nhd\ m$ of the soil substrate from the formula $$\frac{I_r^p}{I_r^s} e^{i\Delta} = \frac{r_m^p}{r_m^s}$$

In the formula, $r_m^p$ and $r_m^s$ are the Fresnel coefficients for the components of the electric field of the reflected train of microwaves in the plane of incidence and normal to it and are functions of $\theta$, $\lambda$ and $n_m$, and the refractive index of the soil substrate $n_m$ is given essentially by the moisture of the soil substrate.

The foregoing as well as other objects, features and advantages of the present invention will become more apparent from the following detailed description when taken in conjunction with the appended drawings.

DESCRIPTION OF THE PREFERRED EMBODIMENTS

Figure 1:
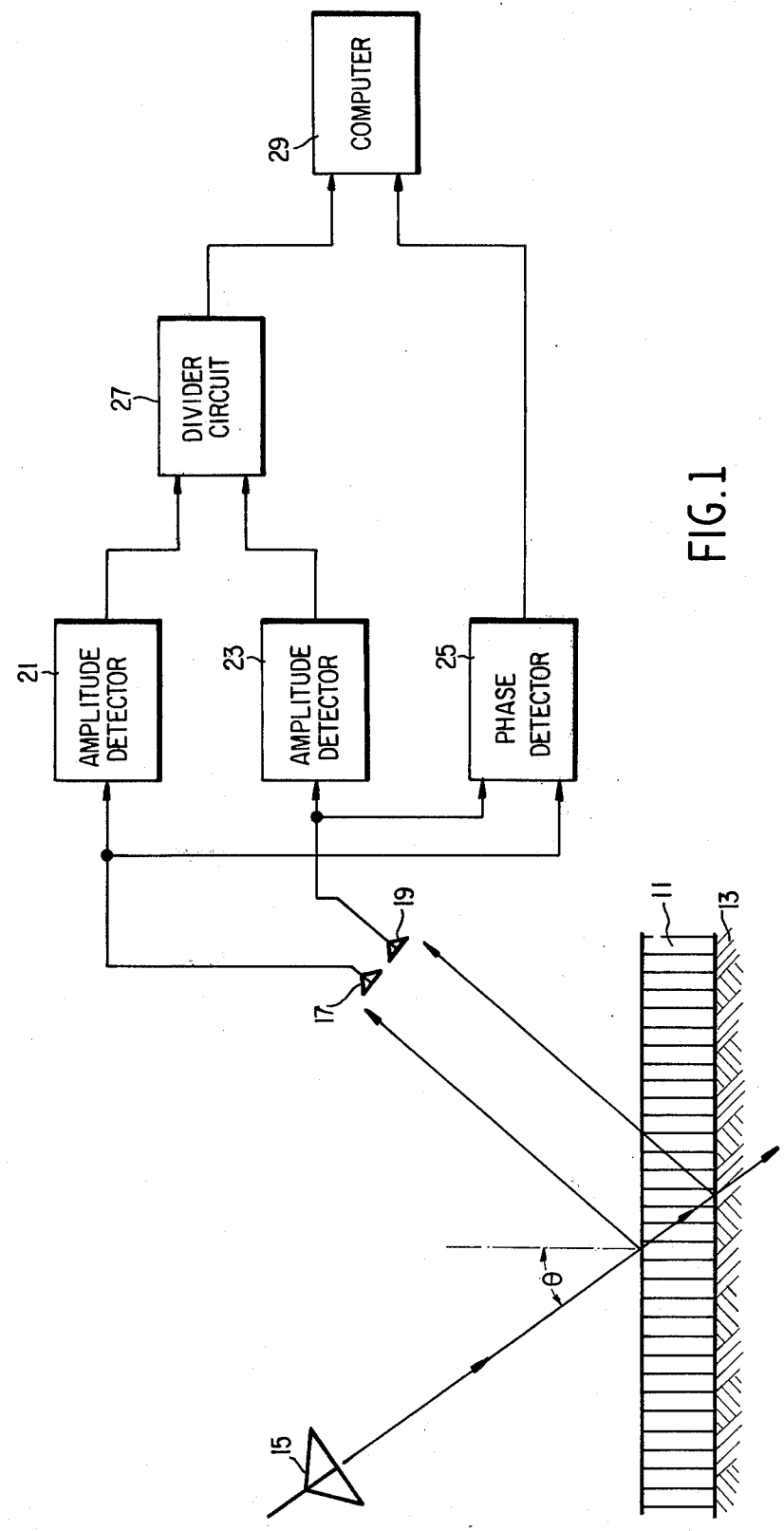
FIG. 1 is a schematic diagram of a first embodiment of a microwave ellipsometry apparatus for carrying out the present invention.

Referring to FIG. 1, a first embodiment of a microwave ellipsometry apparatus for carrying out the inventive method is illustrated. In the Figure, there is shown a layer of vegetation 11 whose mean thickness and electrical properties, in addition to the electrical properties of the soil substrate 13 resting beneath it, are to be determined. The microwave elements are conventional and well-known to those skilled in the art. Radiation from the antenna 15 of a microwave transmitter 15 on a first platform is directed at the vegetation 11 and the soil substrate 13. Reflected energy from the top surface of the vegetation and the interface between the vegetation and the soil substrate is picked up by the antennae 17 and 19 of the microwave receiver on a second platform and detected in the amplitude detectors 21 and 23, and in the phase detector 25. The output of the amplitude detectors is fed to a divider circuit 27. The information received from a divider circuit 27 and the phase detector 25 is analyzed in the computer 29.

Before discussing the operation of the FIG. 1 arrangement, it is in order to consider the Drude theory of the effect of reflection on the state of polarization of a polarized light wave (Ann. Physik 272, 532, 865; Ann. Physik 275, 481). According to this theory, there exists a mathematical relationship between the refractive index of a substrate, the refractive index and thickness of a dielectric film covering the substrate and the reflection coefficients and absolute phase shifts of the two component plane waves of the electric field vector of a polarized light wave reflected from the film covered substrate.

The two parameters correlated with the thickness $d$ and the refractive index $n$ of the dielectric film are $\Psi$ and $\Delta$. The parameter $\Psi = \arctan(r^p/r^s)$ where $r^p$ is the reflection coefficient of the component of the electric field vector in the plane of incidence after reflection, and $r^s$ is the reflection coefficient of the component of the electric field vector normal to the plane of incidence after reflection. The parameter $\Delta = u^p - u^s$, where $u^p$ and $u^s$ are the absolute phase shifts of the same components brought about by the reflection.

The effect of reflection from a film covered substrate on the intensities and phases of the components of the electric field vector depends on interference between the light wave reflected from the air-film interface and the light waves refracted into the air after each of an infinite number of reflections between the film-substrate and the film-air interfaces. Thus, the relationships between the properties of the reflecting systems and $\Psi$ and $\Delta$ are derived in terms of the Fresnel reflection coefficients for the component plane waves of the electric field vector at the two interfaces and the optical thickness of the film. The resulting fundamental relationship is given by formula (A), namely, $$\frac{I_r^{p,s}}{I_i^{p,s}} e^{iu^{p,s}} = \frac{\left(r_f^{p,s} + r_m^{p,s}\exp(-i4\pi\sqrt{n_f^2-\sin^2\theta}\, d/\lambda)\right)}{\left(1 + r_f^{p,s}r_m^{p,s}\exp(-i4\pi\sqrt{n_f^2-\sin^2\theta}\, d/\lambda)\right)} \quad (A)$$

In the formula, $I^{p,s}$ represents the intensities of the components of the electric field vector and $u^{p,s}$ represents the corresponding absolute phase shifts. $I_i^{p,s}$ are the intensities of the components before reflection; $r_f^{p,s}$ and $r_m^{p,s}$ are the Fresnel coefficients for reflection at the film and substrate surface, respectively. $d$ is the thickness of the film, $n_f$ its index of refraction, $\theta$ the angle of incidence and $\lambda$ the wave length of the incident light wave. The superscripts, $p$ and $s$ indicate that this formula holds for each component separately. Writing the above formula for the two components $p$ and $s$ separately and taking the ratio, one obtains formula (B), namely, $$\tan\psi \cdot e^{i\Delta} = \frac{\left[r_f^p + r_m^p\exp(-i4\pi\sqrt{n_f^2-\sin^2\theta}\, d/\lambda)\right]}{\left[1 + r_f^p r_m^p\exp(-i4\pi\sqrt{n_f^2-\sin^2\theta}\, d/\lambda)\right]} \cdot \frac{\left[1 + r_f^s r_m^s\exp(-i4\pi\sqrt{n_f^2-\sin^2\theta}\, d/\lambda)\right]}{\left[r_f^s + r_m^s\exp(-i4\pi\sqrt{n_f^2-\sin^2\theta}\, d/\lambda)\right]} \quad (B)$$

where $r_f^p$, $r_m^p$, $r_f^s$, and $r_m^s$ are functions of $\theta$, $\lambda$, $d$ and the refractive indices $n_f$ and $n_m$ of film and substrate respectively. $d$ and $n$ cannot be expressed in closed form in terms of the measurable quantities $\Psi$ and $\Delta$. However, iteration methods are available for use with computers, such as National Bureau of Standards Technical Note 242, which can compute $d$ and $n$ from $\Psi$ and $\Delta$.

Since Drude's theory is based on Maxwell's equations which are valid not only for visible light but for all electromagnetic waves, the correlation between $\Psi$ and $\Delta$ and $n$ and $d$ must be the same in the microwave region as in the optical region. A layer of vegetation on a soil substrate must, therefore, be seen by means of microwaves in a similar way as the thin film on the thick substrate is seen by means of visible light. The height of the vegetation corresponds to the film thickness $d$, whereas the effective refractive index of the vegetation which at microwave frequency is as given essentially by its moisture content corresponds to the refractive index $n$ of the film. The basic difference is that all dimensions are enlarged by a factor between 10,000 and 2,000,000.

In operation of the apparatus of FIG. 1, a train of microwaves emerges circularly polarized from the antenna 15 and is directed toward the vegetation at a predetermined angle of incidence $\theta$. The intensities $I_i^p$ and $I_i^s$ of the orthogonal components of the electric field of the circularly polarized wave in the plane of incidence and normal to it are equal and have a phase difference of 90°. The train of microwaves is reflected from the vegetation 11 and the soil substrate 13. The layer of vegetation can be characterized by a refractive index $n_f$, and has a thickness $d$. The soil can be characterized by a refractive index $n_m$. The two components of the train of microwaves after reflection are received by two orthogonally arranged dipole antennas 17 and 19 and are detected in the amplitude detectors 21 and 23 which measure their intensities $I_r^p$ and $I_r^s$. The phase detector 25 measures the phase difference, 90° + $\Delta$ between the components. The divider circuit 27 determines the ratio of $I_r^p$ to $I_r^s$. This ratio is just equal to tan $\Psi$ since the ratio of $I_i^p$ to $I_i^s$ is unity. The values of tan $\Psi$ and $\Delta$ are then fed to the computer 29 which computes the refractive indices of the vegetation and of the soil substrate, and the thickness of the vegetation according to a computer program such as that described in National Bureau of Standards Technical Note 242.

There may be as many as five unknowns. These include the real part of the dielectric constant of the vegetation $\epsilon_f'$ and the imaginary part of the dielectric constant of the vegetation $\epsilon_f''$ related to the refractive index $n_f$ by the identity $\epsilon_f' - j\epsilon_f'' = n_f^2$; the real part of the dielectric constant of the soil substrate $\epsilon_m'$ and the imaginary part of the dielectric constant of the soil substrate $\epsilon_m''$ related to the refractive index $n_m$ by the identity $\epsilon_m' - j\epsilon_m'' = n_m^2$; and the thickness of the vegetation layer

*d*. Generally, if a single measurement is made, 3 of 5 variables must be known in order to determine the 2 other variables. For example, if there is no vegetation layer, $\epsilon_m'$ and $\epsilon_m''$ can be determined from the formula (B) with $r^{p,s}_f = d = 0$. If the electrical properties of the soil are already known and if the real and imaginary parts of the dielectric constant of the vegetation layer are in a well-known relationship, for example, $\epsilon_f'' = 0$, or generally $\epsilon_f''$ is a function of $\epsilon_f'$ then, $\epsilon_f'$, $\epsilon_f''$ and $d$ can be determined. If only two of the five variables are known, the three other variables can usually be determined by taking measurements at two different angles of incidence $\theta_1$ and $\theta_2$. IT should be noted that $\Psi$ and $\Delta$ are cyclic functions of $\theta$ and $d$. This fact results in ambiguities when $d$ is a large fraction, for example 30% or more, of the wave length. In order to avoid such ambiguities, one has to make measurements either at a long enough wavelength, or at two different wavelengths.

Figure 2:
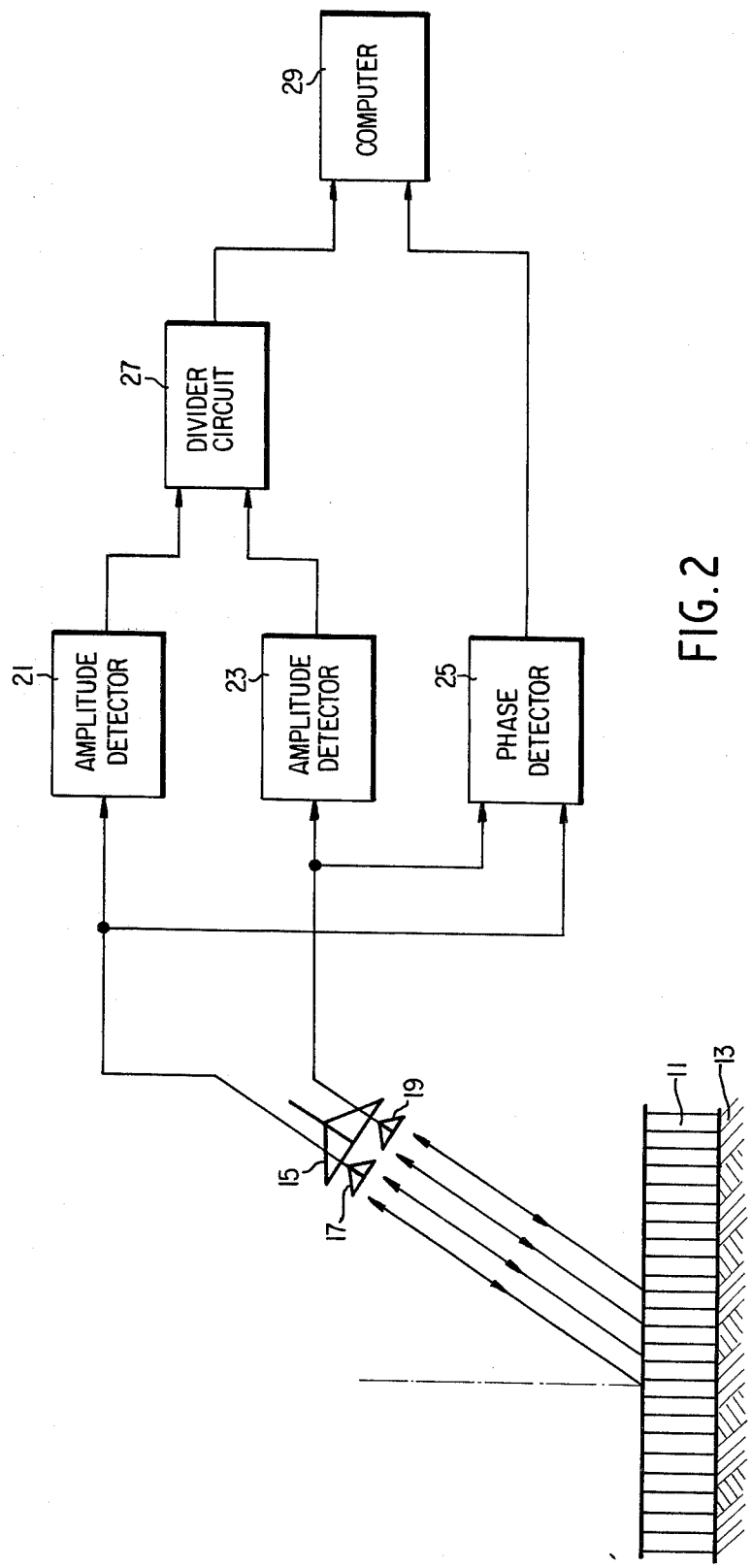
FIG. 2 is a schematic diagram of a second embodiment of a microwave ellipsometry apparatus for carrying out the present invention.

Referring to FIG. 2, a second embodiment of a microwave ellipsometry apparatus for carrying out the inventive method is illustrated. In this instance, the apparatus differs from that shown in FIG. 1 by the inclusion of both transmitter and receiver on the same platform in order that conventional radar equipment may be used for the microwave ellipsometric measurements. Although the transmitter and receiver are now located at the same place with respect to the vegetation surface and not at location symmetrical to the normal of the vegetation surface plane, the electric properties of the vegatation layer and soil substrate can still be determined by the method described in connection with FIG. 1 for the following reason. When the wave length is 1 meter or greater, the incoherent component of the scattered wave is substantially weaker than the coherent component. The formula for calculating both the incoherent and coherent components can be found in the book entitled "Radar Cross Section Handbook," second volume and published by Plenum Press, New York, N.Y., 1970 edition. The coherent component obeys all the rules of ellipsometry, whereas the incoherent component does not. To effectively carry out the method in the second embodiment, it is essential to use a long wave length. The wave length must be at least ten times longer than the mean roughness height of the surface under investigation.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of determining the water content and thickness $d$ of a layer of vegetation on a soil substrate of known refractive index $n_m$ comprising:

transmitting a circularly polarized train of microwaves of wave length $\lambda$ to a layer of vegetation at a predetermined angle of incidence $\theta$, the orthogonal components of the electric field of said microwaves having equal intensities $I_i^p$ and $I_i^s$ and in quadrature in the plane of incidence and normal to it;

receiving the orthogonal components of the train of microwaves reflected from the layer of vegetation and the soil substrate;

detecting the intensities $I_r^p$ and $I_r^s$ of the orthogonal components of the electric field of the received reflected train of microwaves;

determining the ratio $I_r^p/I_r^s$ of the intensities of the detected orthogonal components of the electric field of the received reflected train of microwaves;

measuring the phase difference $90° + \Delta$ of the orthogonal components of the electric field of the received reflected train of microwaves; and computing the refractive index $n_f$ and the thickness $d$ of the layer of vegetation from the formula:

$$\frac{I_r^p}{I_r^s} e^{i\Delta} = \frac{\left[ r_f^p + r_m^p \exp(-i4\pi \sqrt{n_f^2 - \sin^2\theta}\, d/\lambda) \right]}{\left[ 1 + r_f^p r_m^p \exp(-i4\pi \sqrt{n_f^2 - \sin^2\theta}\, d/\lambda) \right]} \cdot \frac{\left[ 1 + r_f^s r_m^s \exp(-i4\pi \sqrt{n_f^2 - \sin^2\theta}\, d/\lambda) \right]}{\left[ r_f^s + r_m^s \exp(-i4\pi \sqrt{n_f^2 - \sin^2\theta}\, d/\lambda) \right]}$$

wherein $r_f^p$, $r_m^p$, $r_f^s$ and $r_m^s$ are the Fresnel coefficients and are functions of $\theta$, $\lambda$, $d$, $n_f$ and $n_m$; and the refractive index of the vegetation $n_f$ is given essentially by the water content of the vegetation.

2. A method of determining the moisture of a soil substrate comprising:

transmitting a circularly polarized train of microwaves of wave length $\lambda$ to a layer of soil substrates at a predetermined angle of incidence, the orthogonal components of the electric field of said microwaves having equal intensities $I_i^p$ and $I_i^s$ and in quadrature in the plane of incidence and normal to it;

receiving the orthogonal components of the train of microwaves reflected from the layer of vegetation and the soil substrate;

detecting the intensities $I_r^p$ and $I_r^s$ of the orthogonal components of the electric field of the received reflected train of microwaves;

determining the ratio $I_r^p/I_r^s$ of the intensities of the detected orthogonal components of the electric field of the received reflected train of microwaves;

measuring the phase difference $90° + \Delta$ of the orthogonal components of the electric field of the received reflected train of microwaves; and computing the refractive index $n_m$ of the soil substrate from the formula $$\frac{I_r^p}{I_r^s} e^{i\Delta} = \frac{r_m^p}{r_m^s}$$

wherein $r_m^p$ and $r_m^s$ are the Fresnel coefficients for the orthogonal components and are a function of $\theta$, $\lambda$, and $n_m$; and the refractive index of the soil $n_m$ is given essentially by the moisture of the soil substrate.

* * * * *